US006512028B1

(12) United States Patent
Gentilcore et al.

(10) Patent No.: US 6,512,028 B1
(45) Date of Patent: Jan. 28, 2003

(54) GEL MATERIALS

(75) Inventors: Giovanni Gentilcore, Swindon (GB); Ali Bekkaoui, Swindon (GB); Ian Michael Lancaster, Clwyd (GB)

(73) Assignee: Scimat Limited (GB)

( * ) Notice: Subject to any disclaimer, the term of this patent is extended or adjusted under 35 U.S.C. 154(b) by 0 days.

(21) Appl. No.: 09/509,397

(22) PCT Filed: Sep. 18, 1998

(86) PCT No.: PCT/GB98/02848

§ 371 (c)(1),
(2), (4) Date: Jun. 1, 2000

(87) PCT Pub. No.: WO99/16812

PCT Pub. Date: Apr. 8, 1999

(30) Foreign Application Priority Data

Sep. 27, 1997 (GB) ............................................. 9720506

(51) Int. Cl.⁷ .............................. C08J 5/10; C08L 3/00; C08L 89/00
(52) U.S. Cl. .............................. 524/47; 524/52; 524/53
(58) Field of Search ............................. 524/52, 53, 47, 524/501

(56) References Cited

U.S. PATENT DOCUMENTS

| 3,419,006 A | 12/1968 | King | 128/268 |
| 3,898,143 A | 8/1975 | Assarsson et al. | 204/159 |
| 5,578,661 A | 11/1996 | Fox et al. | 524/27 |

FOREIGN PATENT DOCUMENTS

| EP | 0 046 136 A2 | 2/1982 |
| GB | 1 392 624 | 4/1975 |
| GB | 2 100 269 A | 12/1982 |
| GB | 2156370 A | 10/1985 |
| JP | 42634 | 2/1993 |
| WO | 96/04025 | 2/1996 |

*Primary Examiner*—James J. Seidleck
*Assistant Examiner*—U K Rajguru
(74) *Attorney, Agent, or Firm*—Lerner, David, Littenberg, Krumholz & Mentlik, LLP

(57) ABSTRACT

Methods of making gel materials are disclosed including mixing a water soluble crosslinkable matrix polymer, a particulate polymer material which has been crosslinked to a gel content of at least 55% and an aqueous solvent, and crosslinking the matrix polymer to form a gel matrix of the matrix polymer in which the particles of particulate polymer material are dispersed, each of the crosslinked matrix polymer and the crosslinked particulate polymer material being capable of absorbing water. Gel materials are also disclosed including particles of a particulate polymer material capable of absorbing water and which is crosslinked so that it has a gel content of at least about 55% dispersed in a matrix of a polymer which has been crosslinked to reduce its solubility in water so that it swells rather than dissolves in water, the size of at least 60% by weight of the particles of particulate polymer material being less than about 100 μm.

21 Claims, No Drawings

GEL MATERIALS

FIELD OF THE INVENTION

The present invention relates to a gel material and to a method of making a gel material.

BACKGROUND OF THE INVENTION

Gels are known materials which have mechanical properties which enable them to be stored without flowing significantly. They can be self-supporting so that a sheet of a gel material can be handled without breaking or tearing. Weaker gel materials can be provided with a support, for example in the form of a fabric, and generally an open weave mesh.

Gel materials can include a component in their composition which enable the materials to absorb water (including water-based liquids). Such a material is sometimes referred to as a hydrogel. It can absorb several times its own weight in water, resulting in significant swelling of the gel. It can be important for many applications for the ability of the gel material to absorb water to be balanced against loss of physical properties due to swelling when the water is absorbed.

U.S. Pat. No. 3,898,143 discloses a method of making a gel material which involves co-crosslinking in aqueous solution an intimate mixture of polyethylene oxide and another water soluble polymer such as hydroxyethyl cellulose. The components of the mixture might be immiscible. However, the mixture is rendered homogeneous (or as a heterogeneous microphase) when the crosslinking reaction takes place, the crosslinking reaction being relied on to preserve the homogeneity of the mixture.

SUMMARY OF THE INVENTION

In accordance with the present invention, a method of making a gel material has been provided which comprises mixing a water soluble crosslinkable matrix polymer, a particulate polymer material which has been crosslinked so that it has a gel content of at least about 55%, and an aqueous solvent to form a mixture, and crosslinking the matrix polymer so as to form a gel matrix of the matrix polymer in which the particles of the particulate polymer material are dispersed, each of the crosslinked matrix polymer and the crosslinked particulate polymer material being capable of absorbing water. In a preferred embodiment, the method includes drying the gel material after the crosslinking of the matrix polymer.

In accordance with one embodiment of the method of the present invention, the particulate polymer material is present in the mixture in an amount of at least about 0.5% by weight.

In accordance with another embodiment of the method of the present invention, the matrix polymer comprises polyethylene oxide. Preferably, the molecular weight of the polyethylene oxide is not more than about $5\times10^6$.

In accordance with another embodiment of the method of the present invention, the particulate polymer material comprises an acrylic acid or an ester or a salt thereof.

In accordance with another embodiment of the method of the present invention, the particulate polymer material comprises a starch.

In accordance with another embodiment of the method of the present invention, the gel content of the particulate polymer material is at least about 75%.

In accordance with another embodiment of the method of the present invention, the size of at least about 60% by weight of the particles of the particulate polymer material is less than about 100 $\mu$m. Preferably, the size of at least about 85% by weight of the particles of the particulate polymer material is less than about 100 $\mu$m.

In accordance with another embodiment of the method of the present invention, the matrix polymer is present in the mixture in an amount of at least about 2% by weight.

In accordance with another embodiment of the method of the present invention, the ratio by weight of the matrix polymer to the particulate polymer material is at least about 0.1. In a preferred embodiment, the ratio by weight of the matrix polymer to the particulate polymer material is not more than about 10.

In accordance with another embodiment of the method of the present invention, the crosslinking of the matrix polymer is initiated by means of ultraviolet radiation.

In accordance with the present invention, a gel material has also been provided which comprises particles of a particulate polymer material which is capable of absorbing water and which is crosslinked so that it has a gel content of at least about 55% dispersed in a matrix of a polymer which has been crosslinked to reduce its solubility in water so that it swells rather than dissolves in water, the size of at least about 60% by weight of the particles of the particulate polymer material being less than about 100 $\mu$m. In a preferred embodiment, the gel content of the particulate polymer material is at least about 75%

In accordance with one embodiment of the gel material of the present invention, the matrix polymer comprises polyethylene oxide. Preferably, the molecular weight of the polyethylene oxide is not more than about $5\times10^6$.

In accordance with another embodiment of the gel material of the present invention, the ratio by weight of the matrix polymer to the particulate polymer is at least about 0.1, and in another embodiment, it is not more than about 10.

In accordance with another embodiment of the gel material of the present invention, the gel material is in the form of a sheet.

In accordance with another embodiment of the gel material of the present invention, the particulate polymer material comprises an acrylic acid or an ester or a salt thereof.

In accordance with another embodiment of the gel material of the present invention, the particulate polymer material comprises a starch.

The present invention provides a gel material in which absorbency is maintained at a high level due to the use of a particulate polymer absorbent material that is crosslinked so that it retains its particulate form, in a matrix of a polymer (especially of a polyethylene oxide) which has been crosslinked so as to reduce its solubility in water so that it swells rather than dissolves in water.

Accordingly, in one aspect, the present invention provides a gel material which comprises particles of a particulate polymer material which is capable of absorbing water and which is crosslinked so that it has a gel content of at least about 55%, and which is supported in a matrix provided by a polymer which has been crosslinked to reduce its solubility in water so that it swells rather than dissolves in water.

The use of a particulate absorbent material in the gel of the present invention is believed to enhance the ability of the material to absorb water (including water based liquids such as solutions) compared with hydrogel compositions in which the matrix and absorbent materials are mixed homogeneously, for example as disclosed in U.S. Pat. No. 3,898,143. Thus, the gel material of the present invention can achieve higher water absorbencies than comparable materials while retaining appropriate physical properties so that it is capable of being handled, prior to and during use. In particular, the gel materials can be manipulated without losing their integrity even when significant quantities of water (or other aqueous materials) have been absorbed.

Preferably, the gel content of the particulate polymer material is at least about 60%, more preferably at least about 75%, for example at least about 90%. Gel content is measured by weighing accurately a sample of dry polymer (weighing about 0.1 g), and placing the sample in a Soxhlet extraction apparatus containing 200 ml of a 25:75 by weight mixture of water and ethanol. After 12 hours of extraction, the sample is placed in a drying oven at 60° C. until dry. The dry weight is recorded. The gel content is then calculated as follows:

$$\text{Gel content (\%)} = \frac{\text{Non-extracted weight}}{\text{original weight}} \times 100$$

A high gel content has the advantage of ensuring that the particles of the polymer retain their particulate structure, at least to a large degree, when exposed to water, for example when a solution technique is used to make the gel material or when the gel is exposed to water in use. The particles of the polymer will generally be capable of being discerned within the matrix of the gel of the present invention, even when dry, using appropriate microscopy techniques (possibly with staining to obtain or to enhance an appropriate contrast) as necessary. The particles of the polymer will generally be clearly discernable to the naked eye when the gel of the present invention has swollen as a result of liquid absorption, for example providing lines of weakness along which the gel material will tend to fracture when subjected to a large tensile strain.

A high gel content in the particulate polymer can also reduce the tendency for crosslinks to form between the particulate polymer material and the matrix material: the ability of the gel of the present invention to absorb significant quantities of water without losing its integrity is believed to arise in part from the substantial absence of crosslinks between the particulate polymer and the matrix polymer.

Preferably, the size of at least about 60% by weight of the particles of the particulate polymer material is less than about 200 μm, more preferably, the size of at least about 85% by weight of the particles of the particulate polymer material is less than about 200 μm. Preferably, the size of at least about 6001 by weight of the particles of the particulate polymer material is less than about 100 μm, more preferably, the size of at least about 85% by weight of the particles of the particulate polymer material is less than about 100 μm. Accurate control of the size of the polymer particles, preferably within these limits, has been found to enable the gel material to absorb significant quantities of liquid without undesirable weakening of the structure of the material due to swelling of the copolymer particles.

Preferably, the ratio by weight of the matrix polymer to the particulate polymer material is at least about 0.05, more preferably at least about 0.1, most preferably at least about 0.2. This can allow the gel material to be made with adequate physical properties to be handled. Preferably, this ratio is not more than about 25, more preferably not more than about 10, for example not more than about 3. This can allow the gel to have suitable strength to be manipulated prior to and during use.

The gel material of the present invention can be made by solution techniques in which a mixture of the matrix material, the particulate polymer and water is formed and then subjected to a treatment in which the matrix material is crosslinked. Accordingly, in another aspect, the present invention provides a method of making a gel material which comprises the steps of mixing a water soluble crosslinkable matrix polymer, a particulate polymer which has 4 been crosslinked so that it has a gel content of at least about 55%, especially at least about 75%, and an aqueous solvent, and crosslinking the matrix polymer so as to form a gel matrix of the matrix polymer in which the particles of the particulate polymer material are dispersed, each of the crosslinked matrix polymer and the crosslinked particulate polymer being capable of absorbing water. As discussed below, the absorbency of the particulate polymer component of the gel material will generally be significantly greater than that of the matrix polymer. The method can include a step of drying the material, at least partially, after the crosslinking step.

The gel material of the present invention can also be made by a melt processing technique in which the matrix material and the particulate polymer are mixed while the matrix material is molten. Accordingly, in a further aspect, the present invention provides a method of making a gel material which comprises the steps of (a) heating a matrix polymer to cause it to melt, (b) mixing the molten matrix polymer with a particulate polymer which is capable of absorbing water, (c) melt forming the mixture of the matrix polymer and the particulate polymer so as to form a matrix of the matrix polymer in which the particles of the polymer material are dispersed, and (d) crosslinking the matrix polymer so as to reduce its solubility in water so that it swells rather than dissolves in water.

The crosslinking reaction of the matrix polymer can be initiated by ionizing radiation, for example by exposure to an electron beam or to gamma radiation. The crosslinking reaction can be initiated by exposure to ultraviolet radiation. The mixture of the matrix polymer and the particulate polymer material will then include an appropriate initiator component such as benzophenone.

The matrix polymer that is used in the present invention will generally be a water soluble polymer when not crosslinked. The formation of crosslinks in the matrix polymer will reduce its solubility in water so that it will tend to swell rather than to dissolve. A particularly preferred polymer for the matrix material is polyethylene oxide. The molecular weight of the polyethylene oxide will preferably be not more than about $5 \times 10^6$. This can have the advantage of providing the gel material with an appropriately low viscosity to enable the material, to be manipulated during manufacture. Preferably, the molecular weight of the polyethylene oxide is at least about 10', especially at least about $10^5$, so that the resulting gel material has adequate tensile properties. An example of a suitable polyethylene oxide has a molecular weight of about $3 \times 10^6$.

Other polymer materials that can be used to provide the matrix of the gel material include polypyrroles, polyvinyl alcohol, polyacrylamides, and polymers of acrylic acid and related acids (including also esters and salts thereof).

Preferably, the particulate polymer comprises one or more of a starch, a polyacrylic acid (including esters and salts thereof), a substituted cellulose (such as hydroxyethyl cellulose, carboxymethyl cellulose, hydroxymethyl cellulose, and hydroxypropyl cellulose), and polyvinyl alcohols.

The particulate polymer can be a homopolymer or a copolymer. For example, a particularly preferred material for the particulate polymer comprises a copolymer of a starch and a polyacrylic acid (including an ester or salt of an acrylic acid). A suitable material is available from Hoechst Celanese under the trade mark COS915.

For the purposes of this invention, a polymer (such as the matrix polymer) is considered to be capable of absorbing water if its fluid absorption capacity is at least 1.0. Preferably, the polymer will have a fluid absorption capacity of at least about 5.0, more preferably at least about 10.0. Fluid absorption capacity of a material is determined by immersing a sample of the material in 200 ml of fluid. The sample will contain about 0.1 g of dry polymer. The fluid absorption capacity can be determined for a dry material (formed by drying the material after the irradiation step) or for a wet material in the condition which results from the irradiation step. Fluids which might be used include deionized water, and 0.3N or 0.9N saline solution. The fluid absorption capacity (FAC) is calculated from the measured changes in the weight of the polymer due to absorption of water, based on the original weight of the material (measured wet or after the material has been dried as discussed above).

$$\text{Fluid absorption capacity} = \frac{\text{Weight of material after absorption}}{\text{Original weight of material}}$$

The FAC of the matrix polymer will generally be at least about 10, preferably at least about 20. An ability of the matrix polymer to absorb water can be important since the resulting swelling of the polymer structure can enable it to withstand stresses which can arise when the particulate polymer swells on absorption of fluid. However, the ability of the matrix polymer to retain integrity when the gel material absorbs fluid can be more important than its ability itself to absorb fluid. The tensile properties of the matrix polymer can be affected by the degree to which it is crosslinked. Preferably, the gel content of the matrix polymer is at least about 30, more preferably at least about 40, especially at least about 50. Preferably, the gel content of the matrix polymer measured in the dry form is not more than about 100, more preferably not more than about 80, most preferably not more than about 70. Generally, the FAC of the matrix polymer will be not more than about 100, and often not more than about 60.

The FAC of the particulate polymer will generally be significantly higher than that of the matrix polymer, both prior to and after the matrix polymer has been crosslinked. The FAC of the particulate polymer based on the original weight of the material measured dry will preferably be at least about 100, more preferably at least about 250, most preferably at least about 500. Preferably the ratio of the FAC of the particulate polymer to that of the matrix polymer in the gel material of the invention will be at least about 2, more preferably at least about 5, especially at least about 10.

The relative amounts of the matrix polymer and the particulate polymer in the gel material of the present invention will be selected according to the desired properties of the gel material including tensile properties, absorbency and so on. A higher proportion of the matrix polymer may be appropriate for applications in which the gel material is required to be capable of significant deformation without rupture. A higher proportion of matrix polymer might be appropriate when relatively big particles of the particulate polymer are used. Preferably, the ratio by weight of the matrix polymer to the particulate polymer material (measured dry) is at least about 0.05, more preferably at least about 0.1, especially at least about 0.5, for example at least about 1.0. Preferably, the ratio by weight of the matrix polymer to the particulate polymer material is not more than about 15, more preferably not more than about 10, especially not more than about 5. In a preferred composition, the ratio by weight of the matrix polymer to the particulate polymer is about 2.0.

When the gel material of the present invention is prepared by the wet technique described above, it will often be preferred for the proportion of the polymer components in the mixture, expressed in terms of the total weight of the polymer components and the water or other aqueous component, to be at least about 1.0%, preferably at least about 2.0%, for example at least about 4.0%. The proportion will generally by less than about 20%, preferably less than about 15%, more preferably less than about 12%, for example less than about 10%.

In the wet technique described above, water will often be appropriate for use as the aqueous solvent. However, it can be preferred for a salt solution to be used instead of water. Suitable salts include NaCl. The solution will generally have a concentration greater than about 0.5N. The concentration will often be less than about 1.5N. The use of a solution of a salt has the advantage that the viscosity of the gel mixture prior to crosslinking of the matrix material can be less than when water is used, perhaps being more like that of a viscous liquid rather than a pourable gel. This can facilitate release of air bubbles from the gel material prior to the crosslinking reaction.

The gel material of the present invention can be constructed in a number of forms to suit particular applications. The material will generally be formed into a form which optimizes contact between the material and the surface from which fluid is to be absorbed. A generally flat form might be appropriate when fluid is to be absorbed from a surface, for example a sheet or a block. A generally elongate form might be appropriate when fluid is to be absorbed from a narrow space such as a channel, for example in the shape of a strand, rod, cord or the like.

The material of the present invention finds particular application in medical applications where it can be desirable to absorb body fluids, for example in wound treatment. An elongate form of the gel material might be appropriate for treatment of a narrow wound such as an incision. A flat form of the gel material might be appropriate for treatment of a graze, burn or similar surface wound.

EXAMPLE 1

Effect of Irradiation Dose 94.0 g of deionized water and 1 g of 1% benzophenone in acetone were placed in a mixing bowl and the mixer was started at low speed. 4.2 g of a particulate starch polyacrylate copolymer (available from Hoechst Celanese under the trade mark COS915) and 1.8 g of a polyethylene oxide, molecular weight $3 \times 10^6$ (available from Union Carbide under the trade mark WSR301) were added slowly with care being taken to avoid the formation of agglomerates. Mixing was continued at reduced speed until the mixture appeared consistent, generally for about 30 minutes.

The resulting gel was then transferred to a jar and allowed to equilibrate for a period of 24 hours.

The size distribution of the starch polyacrylate polymer particles is set out in Table 1.

TABLE 1

| Particle size (μm) | particles (wt %) |
|---|---|
| >850 | 0.1 |
| 106–850 | 1.9 |
| 75–106 | 11.7 |
| 45–75 | 38.8 |
| <45 | 47.6 |

The mixture was transferred to a mold for crosslinking, which was initiated by exposure to light from a 43.5 W.cm$^{-1}$ ultraviolet lamp positioned about 20 cm from the mixture. The crosslinked gel material was allowed to dry in ambient room temperature and humidity conditions with fan assistance. The gel content and fluid absorption capacity (measured after exposure to deionized water and to a 0.3N NaCl solution for 24 hours) of the resulting dry gel materials were measured, and are set out in Table 2.

TABLE 2

| UV exposure (min) | 0 | 1 | 5 | 15 | 30 |
|---|---|---|---|---|---|
| Gel content (%) | 34.65 | 78.24 | 83.68 | 84.96 | 84.97 |
| FAC (water) | — | 210 | 242 | 274 | 281 |
| FAC (0.3 N NaCl) | — | 53 | 49 | 50 | 54 |

It can be seen that both gel content and fluid absorption capacity remain substantially constant with increasing irradiation dose. This can be contrasted with the data contained in Table 1 in U.S. Pat. No. 3,898,143.

EXAMPLE 2

Pro-portion of Polymer Components

A gel material was prepared using the method described above in Example 1, with the gel in the mold being exposed to the UV radiation for 30 minutes and without the step of drying the gel material after the crosslinking step. The relative amounts of the polyethylene oxide and starch polyacrylate polymers were varied. The fluid absorption capacities of the resulting wet sheet materials were measured after exposure to water for 24 hours and are set out in Table 3.

TABLE 3

| Polyox (g) | Starch (g) | FAC |
|---|---|---|
| 6.0 | 0 | 3.4 |
| 4.2 | 1.8 | 13.3 |
| 1.8 | 4.2 | 26.4 |
| 0 | 6.0 | 48.1 |

It can be seen that the fluid absorption capacity is strongly dependent on the amount of the starch polyacrylate copolymer that is present in the gel composition. The substantially linear relationship between these parameters suggests that there are few interactions between the polyethylene oxide and starch polyacrylate copolymer components, in particular no crosslinks.

EXAMPLE 3

Effect of Polymer Amounts

A gel material was prepared using the method described above in Example 2. The total amounts of the polyethylene oxide and starch polyacrylate polymers were varied while maintaining the relative amounts in the ratio by weight 70:30. The physical characteristics of the resulting gel materials are set out in Table 4.

TABLE 4

| Total polymer (g) | Observations |
|---|---|
| 0.5 | Very runny. Contained areas of crosslinked gel in a watery medium. Could not be handled. |
| 1.0 | A solid gel but weak and easily broken. |
| 1.7 | Still too weak to be handled. |
| 3.0 | Sufficient strength to be handled. |
| 6.0 | Strong gel. Can be handled easily when swollen. |

EXAMPLE 4

Effect of Particulate Polymer

A gel material was prepared using the method described above in Example 2. Other materials were used in place of the starch polyacrylate copolymer. The fluid absorption capacities of the resulting gel materials were measured after exposure to water for 24 hours without drying, and are set out in Table 5.

EXAMPLE 5

Alternative Irradiation

A first sample of a gel material was prepared using the method described above in Example 2. A second sample of a gel material was prepared in similar fashion with the exception that the benzophenone was omitted from the composition and the gel material in place in the mould was subjected to gamma radiation to a dose of 25 kGy. The fluid absorption capacity measured after exposure to water for 24 hours without drying, and Young's moduli of the first and second samples are set out in Table 6.

TABLE 6

|  | FAC | Modulus (kN.M$^{-2}$) |
|---|---|---|
| Sample 1 | 21.4 | 0.041 |
| Sample 2 | 12.4 | 0.096 |

TABLE 5

| POLYMER | SOURCE | % < 100 μm | FAC | OBSERVATIONS |
| --- | --- | --- | --- | --- |
| Starch polyacrylate copolymer | Hoechst Celanese (COS915 ™) | 95 | 27.7 | Smooth and strong |
| Starch polyacrylate copolymer | Hoechst Celanese (IM3000 ™) | 3 | 20.8 | Rough, weak |
| Starch polyacrylate Copolymer | Hoechst Celanese (IM3000 ™) | 90 (ground) | 17.3 | Smooth and strong |
| Starch polyacrylamide polyacrylate copolymer (Na salt) | Grain Processing Corp (WATERLOCK A100 ™) | 59 | 3.6 | Quite smooth |
| Starch polyacrylamide polyacrylate copolymer (Na salt) | Grain Processing Corp (WATERLOCK A200 ™) | 24 | — | Disintegrates |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of making a gel material which comprises mixing a water soluble crosslinkable matrix polymer, a particulate polymer material which has been crosslinked so that it has a gel content of at least about 55%, and an aqueous solvent to form a mixture, and crosslinking said matrix polymer so as to form a gel matrix of said matrix polymer in which the particles of said particulate polymer material are dispersed, each of said crosslinked matrix polymer and said crosslinked particulate polymer material being capable of absorbing water.

2. A method as claimed in claim 1, including drying said gel material after said crosslinking of said matrix polymer.

3. A method as claimed in claim 1, wherein said particulate polymer material is present in said mixture in an amount of at least about 0.5% by weight.

4. A method as claimed in claim 1, wherein said matrix polymer comprises polyethylene oxide.

5. A method as claimed in claim 1, wherein said particulate polymer material comprises an acrylic acid or an ester or a salt thereof.

6. A method as claimed in claim 1, wherein said particulate polymer material comprises a starch.

7. A method as claimed in claim 1, wherein the gel content of said particulate polymer material is at least about 75%.

8. A method as claimed in claim 1, wherein the size of at least about 60% by weight of the particles of said particulate polymer material is less than about 100 μm.

9. A method as claimed in claim 8, wherein the size of at least about 85% by weight of the particles of said particulate polymer material is less than about 100 μm.

10. A method as claimed in claim 1, wherein said matrix polymer is present in said mixture in an amount of at least about 2% by weight.

11. A method as claimed in claim 1, wherein the ratio by weight of said matrix polymer to said particulate polymer material is at least about 0.1.

12. A method as claimed in claim 1, wherein the ratio by weight of said matrix polymer to said particulate polymer material is not more than about 10.

13. A method as claimed in claim 1, wherein said crosslinking of said matrix polymer is initiated by means of ultraviolet radiation.

14. A gel material which comprises particles of a particulate polymer material which is capable of absorbing water and which is crosslinked so that it has a gel content of at least about 55% dispersed in a matrix of a polymer which has been crosslinked to reduce its solubility in water so that it swells rather than dissolves in water, the size of at least about 60% by weight of the particles of said particulate polymer material being less than about 100 μm.

15. A gel material as claimed in claim 14, wherein the gel content of said particulate polymer material is at least about 75%.

16. A gel material as claimed in claim 14, wherein said matrix polymer comprises polyethylene oxide.

17. A gel material as claimed in claim 14, wherein the ratio by weight of said matrix polymer to said particulate polymer is at least about 0.1.

18. A gel material as claimed in claim 14, wherein the ratio by weight of said matrix polymer to said particulate polymer material is not more than about 10.

19. A gel material as claimed in claim 14 in the form of a sheet.

20. A gel material as claimed in claim 14, wherein said particulate polymer material comprises an acrylic acid or an ester or a salt thereof.

21. A gel material as claimed in claim 14, wherein said particulate polymer material comprises a starch.

\* \* \* \* \*